(12) United States Patent
Shimada et al.

(10) Patent No.: US 6,591,681 B1
(45) Date of Patent: Jul. 15, 2003

(54) NONDESTRUCTIVE INSPECTION APPARATUS FOR INSPECTING AN INTERNAL DEFECT IN AN OBJECT

(75) Inventors: Takashi Shimada, Tokyo (JP); Shinichi Hattori, Tokyo (JP); Takahiro Sakamoto, Tokyo (JP); Syuichi Nakamura, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/111,168

(22) PCT Filed: Aug. 23, 2000

(86) PCT No.: PCT/JP00/05643

§ 371 (c)(1),
(2), (4) Date: Apr. 22, 2002

(87) PCT Pub. No.: WO02/16925

PCT Pub. Date: Feb. 28, 2002

(51) Int. Cl.$^7$ ............................................. G01N 29/20
(52) U.S. Cl. ........................ 73/600; 73/644; 73/643
(58) Field of Search ....................... 73/598, 600, 643, 73/644, 602

(56) References Cited

U.S. PATENT DOCUMENTS

| | | | | |
|---|---|---|---|---|
| 4,150,576 A | * | 4/1979 | Tarpley, Jr. | 73/594 |
| 4,338,820 A | * | 7/1982 | Jassby et al. | 73/597 |
| 4,947,851 A | * | 8/1990 | Sarvazyan et al. | 600/438 |
| 5,585,546 A | * | 12/1996 | Gururaja et al. | 73/1.82 |
| 5,612,495 A | | 3/1997 | Shimada et al. | |
| 6,371,051 B1 | * | 4/2002 | Klein et al. | 119/200 |

FOREIGN PATENT DOCUMENTS

| | | | | |
|---|---|---|---|---|
| JP | 21558 | * | 2/1983 | 73/620 |
| JP | 90058 | * | 3/1990 | 73/597 |
| JP | 291962 | * | 12/1990 | 73/597 |
| JP | 8-21824 | | 1/1996 | |

* cited by examiner

Primary Examiner—Daniel S. Larkin
Assistant Examiner—Nashmiya Fayyaz
(74) Attorney, Agent, or Firm—Sughrue Mion, PLLC

(57) ABSTRACT

A nondestructive inspection apparatus includes a vibrating section 11 which is adapted to be placed in pressure contact with a surface of a measuring object 16 for generating an acoustic elastic wave W, a receiving section 12 for receiving a reflected wave, a pushing mechanism 13 for pushing the vibrating section and the receiving section against the measuring object, a pushing force measurement section 14 for detecting pushing forces Fa, Fb during vibration, a vibration control section 10 for driving the vibrating section, and a reception signal processing section 15 for determining the internal defect based on a reception signal R. The reception signal processing section includes a reflection energy calculation section for calculating a reflection energy level due to elasticity vibration of the measuring object, a reflection energy correction section for normalizing the reflection energy level by the pushing force to calculate a correction value; and an internal defect determination section for detecting the internal defect based on the correction value. With this arrangement, the absolute reflection energy level of the reflected wave is determined through comparison, thereby making it possible to improve the evaluation accuracy of the internal defect to a substantial extent.

16 Claims, 11 Drawing Sheets

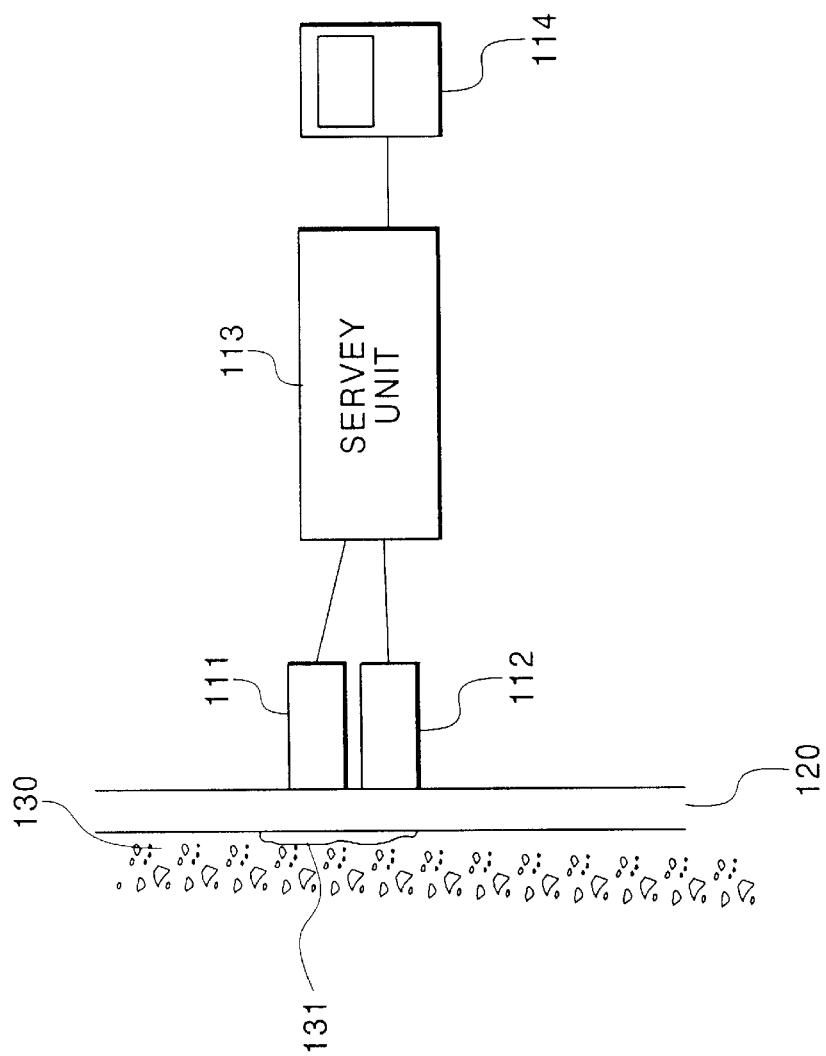

NONDESTRUCTIVE INSPECTION APPARATUS FOR INSPECTING AN INTERNAL DEFECT IN AN OBJECT

TECHNICAL FIELD

The present invention relates to a nondestructive inspection apparatus capable of inspecting an internal defect existing in a measuring object such as a concrete structure, and more particularly it relates to a nondestructive inspection apparatus which enables the diagnosis of internal defects with high reliability by correcting the reflection energy level of an acoustic elastic wave in the form of a vibration wave with high accuracy.

BACKGROUND ART

In the past, hammering tests from an external surface using a hammer have been widely practiced in order to detect internal defects existing in a concrete structure for instance for the reason of convenience and facilitation.

However, when such a well-known hammering test method is used, the accuracy of tests depends on the operator's ability and the level of his or her skill, and it is extremely difficult to carry out hammering by a constant force at all times. In addition, there has been a problem in that the criterion for determination depends greatly on the operator's experience and intuition, so the result of diagnosis becomes vague, making it impossible to achieve sufficient reliability.

Thus, in order to obviate the above problem, there have been proposed a variety of kinds of improved nondestructive inspection apparatuses.

FIG. 11 is a block diagram illustrating a known nondestructive inspection apparatus described for instance in Japanese Patent Application Laid-Open No. 8-21824 to which a method of inspecting defective fillings is applied.

In FIG. 11, the nondestructive inspection apparatus includes a wave transmitting probe 111 which constitutes an acoustic wave transmitting section, a wave receiving probe 112 which constitutes an acoustic wave receiving section, a survey unit 113 having an acoustic wave transmitter, and an FFT analyzer 114 which executes calculation processing by using fast Fourier transform.

Also, a nondestructive inspection object (i.e., an object to be subjected to nondestructive inspection) is provided with a plate member 120 against which the wave transmitting probe 111 and the wave receiving probe 112 are adapted to be placed into abutment, and a filler 130 such as concrete, etc., arranged in the plate member 120. The filler 130 includes a filling defective portion 131 such as a crack, a void, etc., as shown in FIG. 11.

Now, reference will be made to a method of inspecting defective fillings carried out according to the known nondestructive inspection apparatus illustrated in FIG. 11.

First of all, the wave transmitting probe 111 for acoustic wave transmission and the wave receiving probe 112 for acoustic wave reception are placed into abutment against a surface of the plate member 120, as shown in FIG. 11, and an acoustic wave having a wide-band frequency component is repeatedly transmitted from the survey unit 113 through the wave transmitting probe 111.

As a result, the acoustic wave transmitted from the wave transmitting probe 111 is repeatedly sent from the surface of the plate member 120 toward the filler 130.

The wave receiving probe 112 receives a reflected wave of the acoustic wave transmitted from the wave transmitting probe 111 and converts it into a corresponding electric signal, which is then input to the FFT analyzer 114 through the survey unit 113.

The FFT analyzer 114 carries out Fourier analysis of the reception signal and outputs a frequency spectrum level thus obtained to a CRT display (not shown), etc.

Accordingly, an operator can measure the frequency spectrum level output by the FFT analyzer 114 so as to determine the presence or absence of the filling defective portion 131.

With the known nondestructive inspection apparatus as constructed above, if each of the probes 111, 112 is not in contact with the surface of the plate member 120, which acts as a measuring surface, in a satisfactory manner, there would be generated attenuation of the acoustic elastic wave between the wave transmitting probe 111 (vibrating section) or the wave receiving probe 112 (receiving section) and the contact surface (measuring surface) of the plate member 120, thus making it difficult to accurately measure the reflection energy level.

Particularly, the surface condition of the concrete structure is variously changed depending upon the environment where it is placed, so there will likely arise a situation that each of the probes 111, 112 is not able to contact the measuring surface to any satisfactory extent. Such a situation may be considered to include the cases wherein the measuring surface is rugged, or is deteriorated by weathering, or is attached by dust or the like for example.

Moreover, in cases where the respective probes 111, 112 are manually pushed against the measuring surface, the ruggedness of the measuring surface and the condition of attachment of foreign matters greatly influence the contact forces, thereby further reducing the accuracy of measurements by the use of the level of the reflected wave.

In addition, with the known nondestructive inspection apparatus, in cases where a measuring object is changed, or the condition of the contact surface varies with the lapse of time, it would be impossible to make comparison of reflected waves, and hence it has been difficult to evaluate different objects through comparison or by following or tracing changes thereof over time.

Furthermore, since the reflection energy level of the reflected wave cannot be compared by using a constant criterion, there has been a problem that it is impossible to determine a correlation between the distance of the filling defective portion 131 of the filler 130 to the reflection surface and the reflection energy level.

The present invention is intended to obviate the problems as referred to above, and has for its object to provide a nondestructive inspection apparatus which can infer the condition of the contact of a vibrating section and a receiving section with a measuring surface thereby to correct a criterion, and enable the comparison of the absolute reflection energy level even if there is poor contact of the vibrating section and the receiving section with the measuring surface, thus substantially improving the accuracy of measurement of the reflection energy level irrespective of the surface condition of a measuring object and at the same time making it possible to calculate the distance of an internal defect in the measuring object from the measuring surface thereof by using a correlation between the distance from the surface to a filling defective portion (internal defect) in the measuring object and the reflection energy level.

DISCLOSURE OF THE INVENTION

The present invention resides in a nondestructive inspection apparatus for diagnosing an internal defect of a measuring object by injecting an acoustic elastic wave into the measuring object, the apparatus comprising: a vibrating section which is adapted to be placed in pressure contact with a surface of the measuring object for generating the acoustic elastic wave; a receiving section which is adapted to be placed in pressure contact with a surface of the measuring object for receiving a reflected wave of the acoustic elastic wave; a pushing mechanism for pushing the vibrating section and the receiving section against the surface of the measuring object; a pushing force measurement section for detecting pushing forces of the vibrating section and the receiving section against the surface of the measuring object during vibration thereof; a vibration control section for driving the vibrating section thereby to generate the acoustic elastic wave; and a reception signal processing section for determining the internal defect based on the reception signal from the receiving section; wherein the reception signal processing section comprises: a reflection energy calculation section for calculating a reflection energy level due to elasticity vibration of the measuring object based on the reception signal; a reflection energy correction section for normalizing the reflection energy level by the pushing force to calculate a correction value; and an internal defect determination section for detecting the internal defect based on the correction value.

Moreover, the vibrating section according to the nondestructive inspection apparatus of the present invention includes a magnetostrictive vibrator for generating the acoustic elastic wave through a magnetostriction phenomenon.

In addition, the acoustic elastic wave according to the nondestructive inspection apparatus of the present invention comprises a chirp wave with its frequency continuously changing with time; the reception signal processing section includes an envelope detecting section for determining an envelope of elasticity vibration caused by the reflection of the chirp wave, the envelope detecting section being operable to calculate, based on the envelope, a resonance frequency according to a natural oscillation characteristic of the measuring object; and the internal defect determination section detects the internal defect based on the resonance frequency and a response waveform of the supply frequency.

Further, the internal defect determination section according to the nondestructive inspection apparatus of the present invention calculates a distance to the internal defect based on a correlation between a distance to the internal defect and the correction value which is prepared in advance.

Furthermore, the correlation between the distance to the internal defect and the correction value according to the nondestructive inspection apparatus of the present invention is stored in advance in the internal defect determination section as map data of actual measurement values corresponding to the measuring object.

Still further, the reflection energy correction section according to the nondestructive inspection apparatus of the present invention calculates an additional correction value by dividing the correction value by an abnormal range area of the internal defect; and the internal defect determination section calculates the distance to the internal defect based on a correlation between the distance to the internal defect and the additional correction value which is prepared in advance.

Moreover, the correlation between the distance to the internal defect and the additional correction value according to the nondestructive inspection apparatus of the present invention is stored in advance in the internal defect determination section as map data of actual measurement values corresponding to the measuring object.

In addition, the measuring object according to the nondestructive inspection apparatus of the present invention comprises a concrete structure.

BRIEF DESCRIPTION OF THE DRAWING

FIG. 11 is a block diagram illustrating a known nondestructive inspection apparatus.

THE BEST MODE FOR IMPLEMENTING THE INVENTION

Embodiment 1

Hereinafter, a first embodiment of the present invention will be described based on the accompanying drawings.

Figure 1:
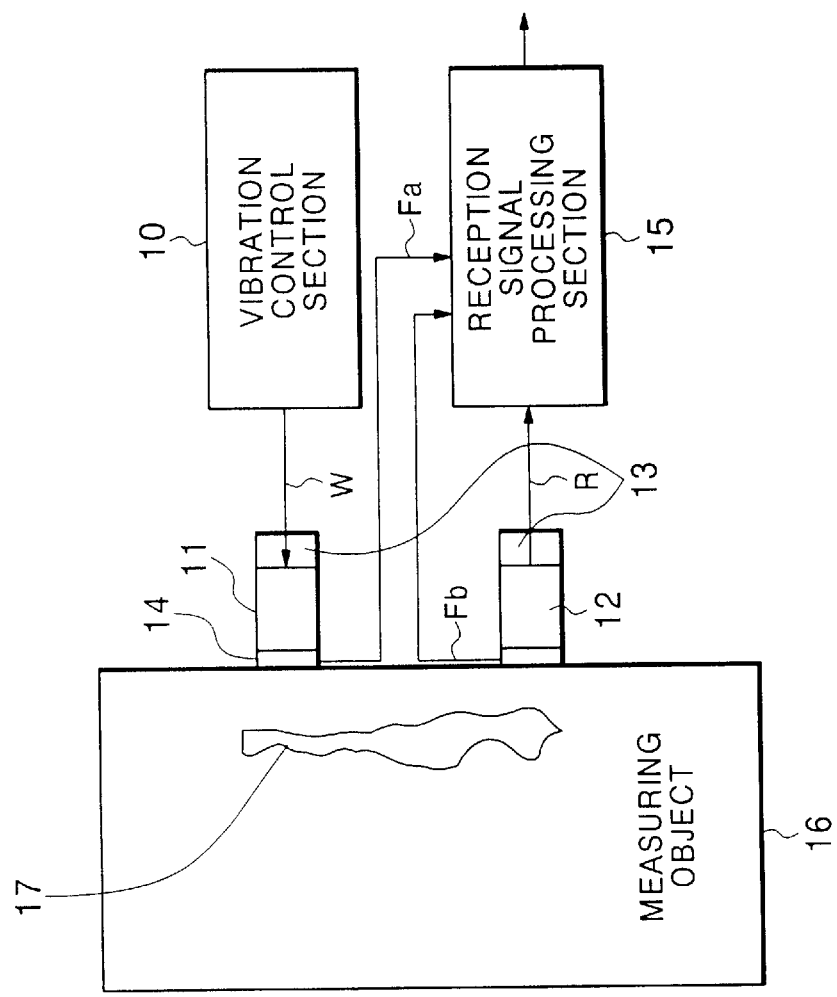
FIG. 1 is a block diagram illustrating a first embodiment of the present invention.

FIG. 1 is a block diagram illustrating the first embodiment of the present invention.

In FIG. 1, a nondestructive inspection apparatus according to the present invention includes a vibration control section 10 for generating a drive signal W to produce an acoustic elastic wave of an audible frequency region, a vibrating section 11 for generating the acoustic elastic wave according to the drive signal W, a receiving section 12 having a reception sensor for detecting a reflected wave of the acoustic elastic wave, a pushing mechanism 13 provided on the rear ends of the vibrating section 11 and the receiving section 12, pushing force measurement sections 14 each having a pressure sensor for detecting pushing or urging forces Fa, Fb at the tip ends of the vibrating section 11 and the receiving section 12, respectively, and a reception signal processing section 15 for performing calculation or arithmetic processing of a reception signal R from the receiving section 12.

The measuring object 16 has an internal defect 17 (void, crack, peeling off, etc.) corresponding to the above-mentioned filling defective portion 131 (see FIG. 11), and the vibrating section 11 and the receiving section 12 are pushed or pressed against a surface (measuring surface) of the measuring object 16 by the pushing or urging force of the pushing mechanism 13.

The pushing or urging forces Fa, Fb of the vibrating section 11 and the receiving section 12 during vibration are detected by the pushing force measurement sections 14, and input to the reception signal processing section 15 together with the reception signal R.

Here, note that the pushing forces Fa, Fb are adjusted to become an equal pushing force F with each other.

Moreover, measurement gauges or the like for measuring the pushing reactive forces at the tip ends of the vibrating section 11 and the receiving section 12 for instance are used as the pushing force measurement sections 14.

In addition, a display (not shown) for displaying the result of determination about the internal defect 17, etc., is connected with the reception signal processing section 15.

Figure 2:
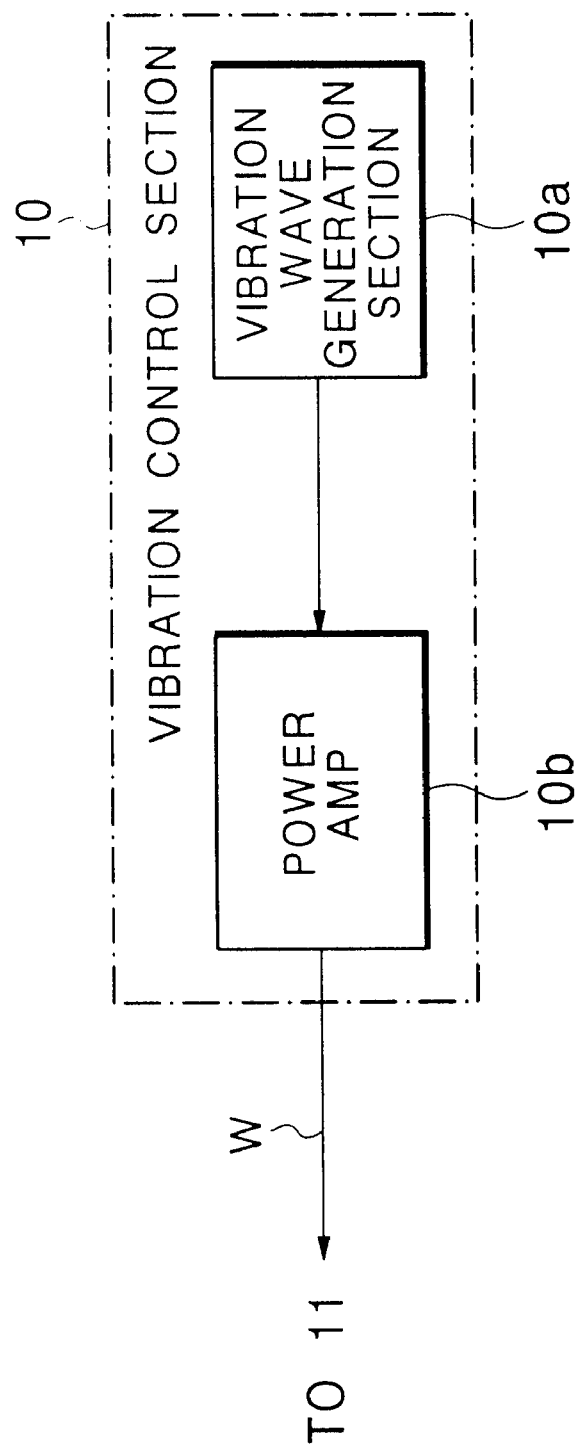
FIG. 2 is a block diagram illustrating a vibration control section according to the first embodiment of the present invention.

FIG. 2 is a block diagram illustrating a concrete example of the vibration control section 10 in FIG. 1.

In FIG. 2, the vibration control section 10 includes a vibration wave generation section 10a for generating a drive signal W to the vibrating section 11, and a power amplifier 10b for amplifying the drive signal W from the vibration wave generation section 10a and imposing it on the vibrating section 11.

Figure 3:
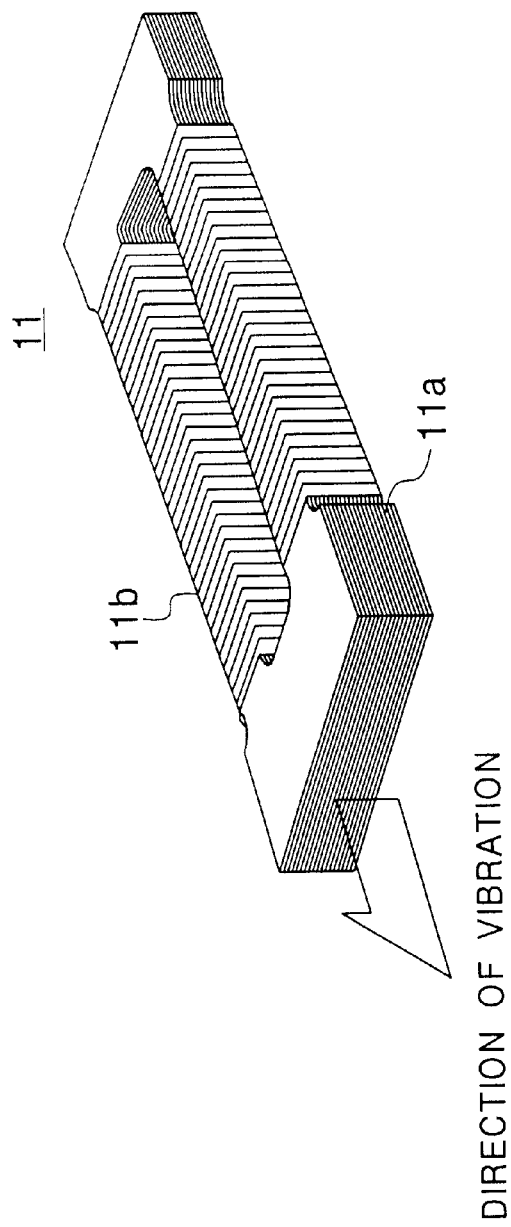
FIG. 3 is a perspective view illustrating a vibrating section according to the first embodiment of the present invention.

FIG. 3 is a perspective view illustrating a concrete example of the configuration of the vibrating section 11 in FIG. 1.

In FIG. 3, the vibrating section 11 is provided with a magnetostrictive vibrator 11a in the shape of a closed-loop core constituted by laminated magnetostrictive elements, and excitation windings 11b wound round two opposed side portions of the magnetostrictive vibrator 11a. The magnetostrictive vibrator 11a vibrates in a direction passing through two sides (see an arrow) of the vibrating section 11 around which the excitation windings 11b are not wound.

Figure 4:
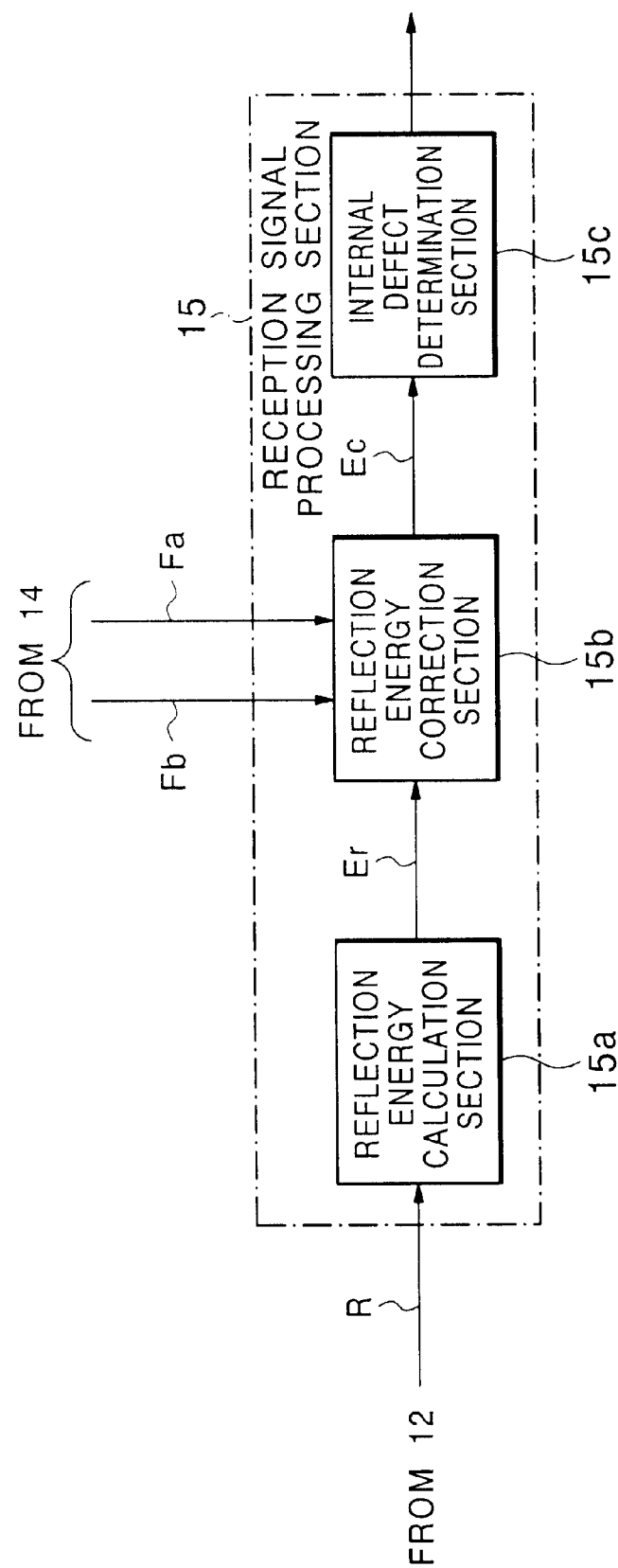
FIG. 4 is a block diagram illustrating a reception signal processing section according to the first embodiment of the present invention.

FIG. 4 is a block diagram illustrating a concrete example of the reception signal processing section 15 in FIG. 1.

In FIG. 4, the reception signal processing section 15 includes a reflection energy calculation section 15a for calculating a reflection energy level Er based on the reception signal R of the reflected wave, a reflection energy correction section 15b for correcting the reflection energy level Er by using the pushing forces Fa, Fb, and an internal defect determination section 15c for determining the presence or absence of an internal defect based on a corrected reflection energy level correction value Ec.

Figure 5:
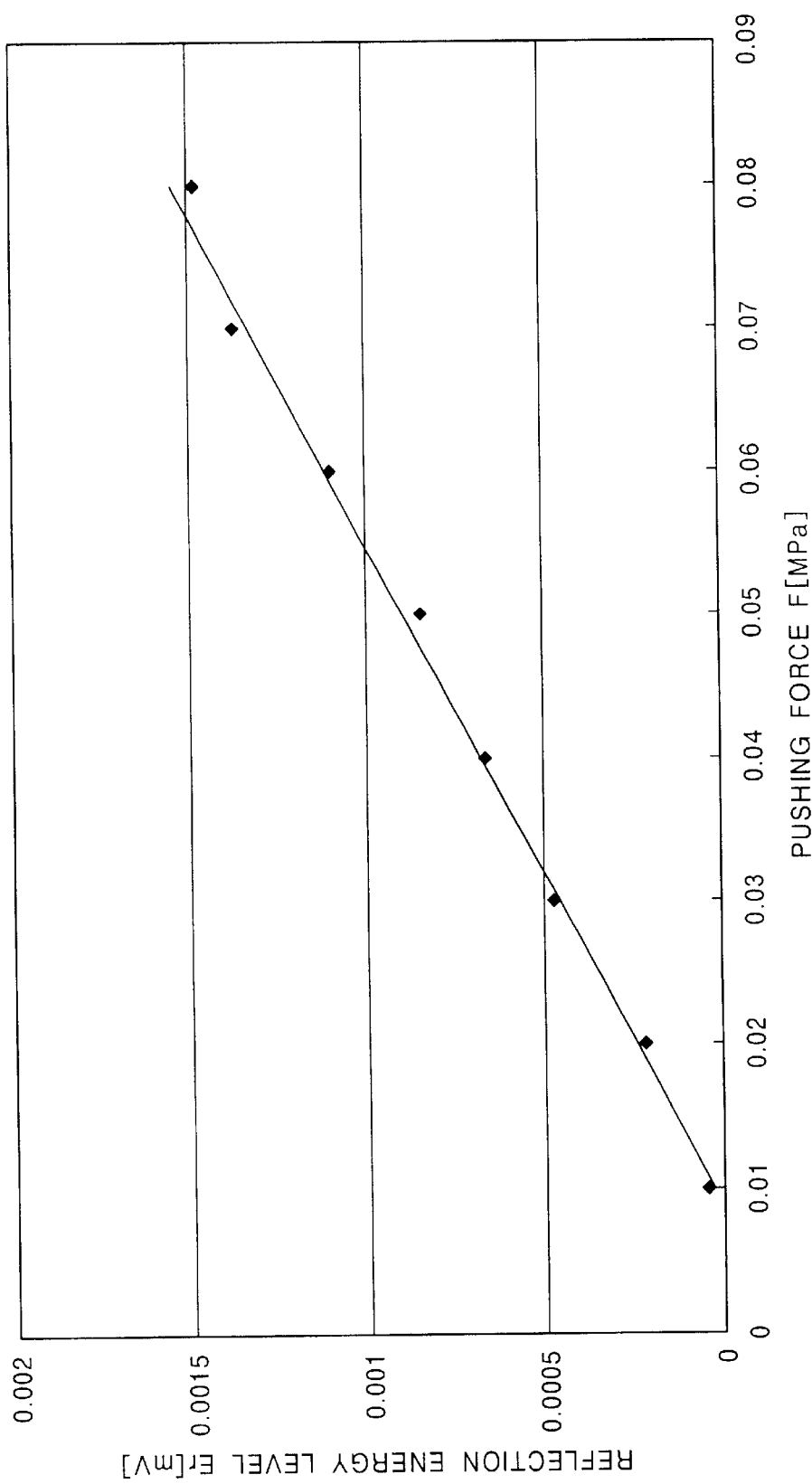
FIG. 5 is a characteristic view illustrating the correlation between a pushing force and a reflection energy level according to the first embodiment of the present invention.

FIG. 5 is a characteristic view illustrating the correlation between the reflection energy level Er and the pushing force F according to the first embodiment of the present invention, the correlation being stored in advance as map data in the reflection energy correction section 15b for instance.

In FIG. 5, the axis of abscissa represents the pushing force F [MPa], and the axis of ordinate represents the reflection energy level Er [mV].

Next, reference will be made to the operation of the first embodiment of the present invention while referring to FIG. 1 through FIG. 5.

In FIG. 1, first of all, the vibration control section 10 drives the vibrating section 11 by means of a drive signal W (a drive current of a predetermined frequency) to generate an acoustic elastic wave.

The vibration control section 10 is comprised of the vibration wave generation section 10a and the power amplifier 10b, as illustrated in FIG. 2, and the vibration wave generation section 10a generates a current waveform in a band corresponding to the characteristic frequency (determined in accordance with the materials of the measuring object 16, the distance to the internal defect 17 therein, etc.), and outputs this to the power amplifier 10b as the drive signal W.

The power amplifier 10b amplifies the drive signal W and outputs it by adjusting the drive signal W to a current value (or voltage value) suitable for driving the vibrating section 11.

The vibrating section 11 is comprised of the magnetostrictive vibrator 11a which forms a core, and the excitation windings 11b which generate a magnetic field in the magnetostrictive vibrator 11a, as illustrated in FIG. 3, and the magnetostrictive vibrator 11a has such a characteristic as to cause a distortion (magnetostriction phenomenon) according to the magnitude and frequency of the magnetic field generated.

Accordingly, when the drive signal W is imposed on the excitation windings 11b, there is generated a magnetic field in the magnetostrictive vibrator 11a so that the magnetostrictive vibrator 11a generates an acoustic elastic wave under the action of the above-mentioned magnetostriction phenomenon.

At this time, the response speed of the magnetostrictive vibrator 11a to a change in the magnetic field is several micro seconds or less, and hence it is within a range in which the magnetostrictive vibrator 11a can follow or trace a current change in an audible frequency range.

Moreover, an acoustic elastic wave of this frequency band can be efficiently generated by supplying a drive signal W in the audible frequency range.

In addition, the magnitude of the magnetic field generated in the vibrating section 11 changes depending on the magnitude and the frequency of the imposed drive signal W, so the amount of distortion of the magnetostrictive vibrator 11a can be adjusted by controlling the current value of the drive signal W.

The core of the vibrating section 11 (magnetostrictive vibrator 11b in FIG. 3) is caused to generate a distortion in accordance to the current value of the imposed drive signal W, whereby an acoustic elastic wave (vibration wave) is injected into the measuring object 16 from the contact portion of the core with the measuring object 16.

The acoustic elastic wave injected from the vibrating section 11 diffuses while being attenuated under the damping effect during propagation in the measuring object 16.

When the acoustic elastic wave during the propagation in the measuring object 16 reaches an acoustic reflection surface of the internal defect 17 (foreign matter, crack, etc.), it is reflected by and penetrates through an interface of the acoustic reflection surface.

In the interface of such an acoustic reflection surface, the greater the contrast of the acoustic propagation speed, it becomes more difficult for the acoustic elastic wave to penetrate, so there is developed a large reflection wave. For instance, in the case of a crack or void which is in contact with air at the back side of the acoustic reflection surface, the most amount of energy of the acoustic elastic wave propagated is reflected at the interface.

On the other hand, in the case of the measuring object 16 within which there exists no acoustic reflection surface, the acoustic elastic wave injected from the measuring surface propagates in the interior of the measuring object 16 so that reflection waves are generated at the opposed surface of the measuring surface and the side surfaces of the measuring object.

In this manner, the reflected waves, which have propagated through the interior of the measuring object 16 to be reflected from the opposed surface and the side surfaces thereof, have been influenced by the attenuation and diffusion of the acoustic elastic wave more greatly than the reflected wave from the internal defect 17 has. As a result, the amplitude of the reflected wave from the measuring object 16 without any internal defect 17 becomes smaller than that in the case where there exists a reflection surface (internal defect 17) inside the measuring object.

Thus, the receiving section 12 is made into contact with a surface (measuring surface) of the measuring object 16 to detect a reflected wave from the acoustic reflection surface, whereby it is possible to determine the presence or absence, the magnitude, etc., of an acoustic reflection surface (internal defect 17).

That is, the reflection energy calculation section 15a in the reception signal processing section 15 performs the time integration of the reception signal R to provide a reflection energy level Er, and the reflection energy correction section calculates a reflection energy level correction value Ec.

Therefore, the internal defect determination section 15c can determine whether an acoustic reflection surface exists in the interior of the measuring object, by making a comparison between the case of the presence of the internal defect 17 (acoustic reflection surface) and the case of the absence thereof based on the reflection energy level correction value Ec.

However, there is a correlation between the pushing forces F (Fa, Fb) of the vibrating section 11 and the receiving section 12 against the surface of the measuring object 16 and the reflection energy level Er based on the reception signal R, as illustrated in FIG. 5.

As is clear from FIG. 5, the reflection energy level Er changes like a linear function according to the pushing forces F, and when the pushing forces F are not sufficient, the expected reflection energy level Er can not be observed, and hence it is impossible to accurately determine the reflection energy level Er corresponding to the actual reflection wave.

Accordingly, the vibrating section 11 and the receiving section 12 are urged or pushed against the surface (measuring surface) of the measuring object 16 by means of the pushing mechanism 13, and the contact pressures (pushing forces F) between the vibrating section 11 and the receiving section 12 and the measuring surface are measured by the pushing force measurement sections 14, and the results of the measurements are input to the reception signal processing section 15, whereby it becomes possible for the reception signal processing section 15 to carry out the estimating or inferring calculation of the reflection energy level correction value Ec normalized according to the pushing forces F.

As a result, the reflection energy level Er can be corrected by using the values of the pushing forces F even if there are not generated enough pushing forces F, thus making it possible to estimate or infer the reflection energy level correction value Ec.

That is, the reception signal processing section 15 corrects through normalization the reflection energy level Er by the pushing forces F based on the reception signal R and the pushing forces F, and makes a determination of the internal defect 17 based on the reflection energy level correction value Ec.

First of all, the reflection energy calculation section 15a in the reception signal processing section 15 (see FIG. 4) calculates the reflection energy level Er detected by the receiving section 12, and inputs the result of the calculation to the reflection energy correction section 15b.

The reflection energy correction section 15b corrects the reflection energy level Er by using the pushing forces F of the vibrating section 11 and the receiving section 12 (the value of Fa or Fb) measured by the pushing force measurement sections 14, and inputs the reflection energy level correction value Ec to the internal defect determination section 15c.

The internal defect determination section 15c informs the operator of the determination result by displaying it from the characteristic of the internal defect 17 prepared in advance, based on the reflection energy level correction value Ec.

In this manner, by estimating and correcting the extent or degree of contact of the vibrating section 11 and the receiving section 12 with the measuring surface based on the pushing forces F, it is possible to determine through comparison the absolute reflection energy level of the acoustic elastic wave irrespective of the surface condition of the measuring object 16. Thus, the accuracy in the evaluation of the internal defect 17 based on the reflection energy level correction value Ec can be greatly improved.

Embodiment 2

A mere acoustic elastic wave has been used as a vibration wave in the above-mentioned first embodiment, but instead there may be used an acoustic elastic wave comprising a chirp wave of which the frequency is changed over time.

Figure 6:
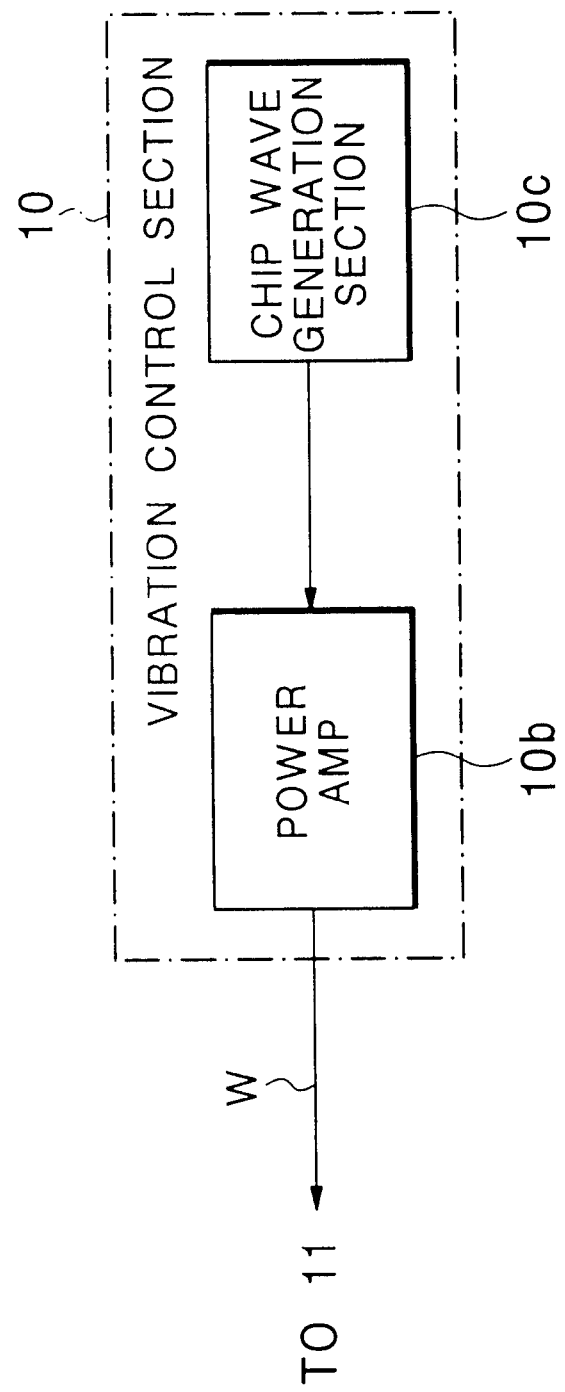
FIG. 6 is a block diagram illustrating a vibration control section according to the second embodiment of the present invention.

FIG. 6 is a block diagram illustrating a vibration control section 10 for generating a chirp wave as an acoustic elastic wave, wherein the same or like components as those in the aforementioned embodiment (see FIG. 2) are identified by the same symbols while omitting a detailed description thereof.

In FIG. 6, a chirp wave generation section 10c corresponds to the above-mentioned vibration wave generation section 10a, and serves to generate a drive signal W comprising a chirp wave.

Figure 7:
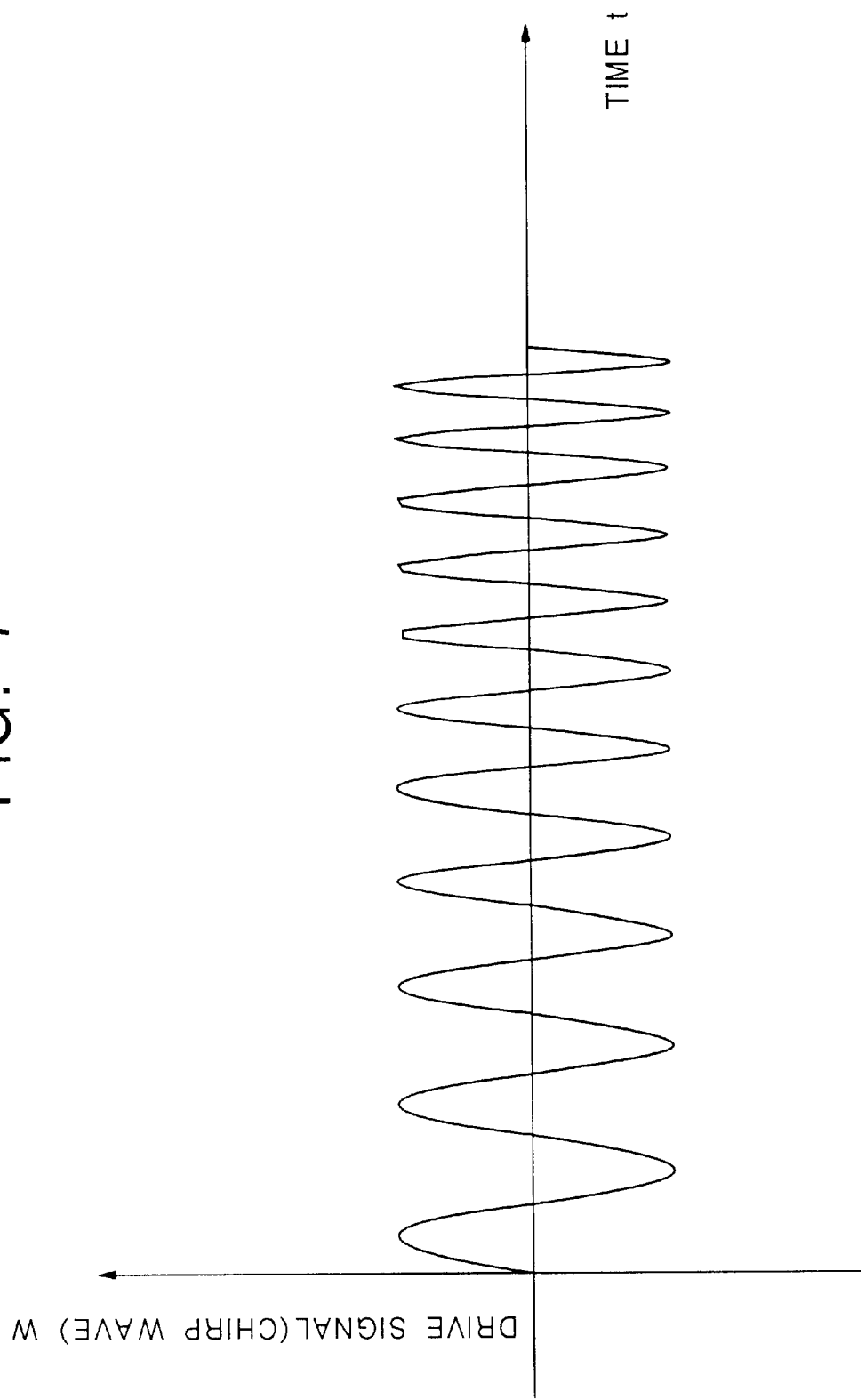
FIG. 7 is a waveform view illustrating an acoustic elastic wave output from the vibration control section according to the second embodiment of the present invention.

FIG. 7 is a waveform view illustrating the drive signal W (chirp wave) output from the vibration control section 10 to the vibrating section 11.

In FIG. 7, the axis of abscissa represents time t, and the axis of ordinate represents the current value of the drive signal W, wherein the frequency of the drive signal W comprising the chirp wave continuously increases with the lapse of time t. Incidentally, contrary to FIG. 7, there can be used a chirp wave of which the frequency continuously decreases with the lapse of time.

Figure 8:
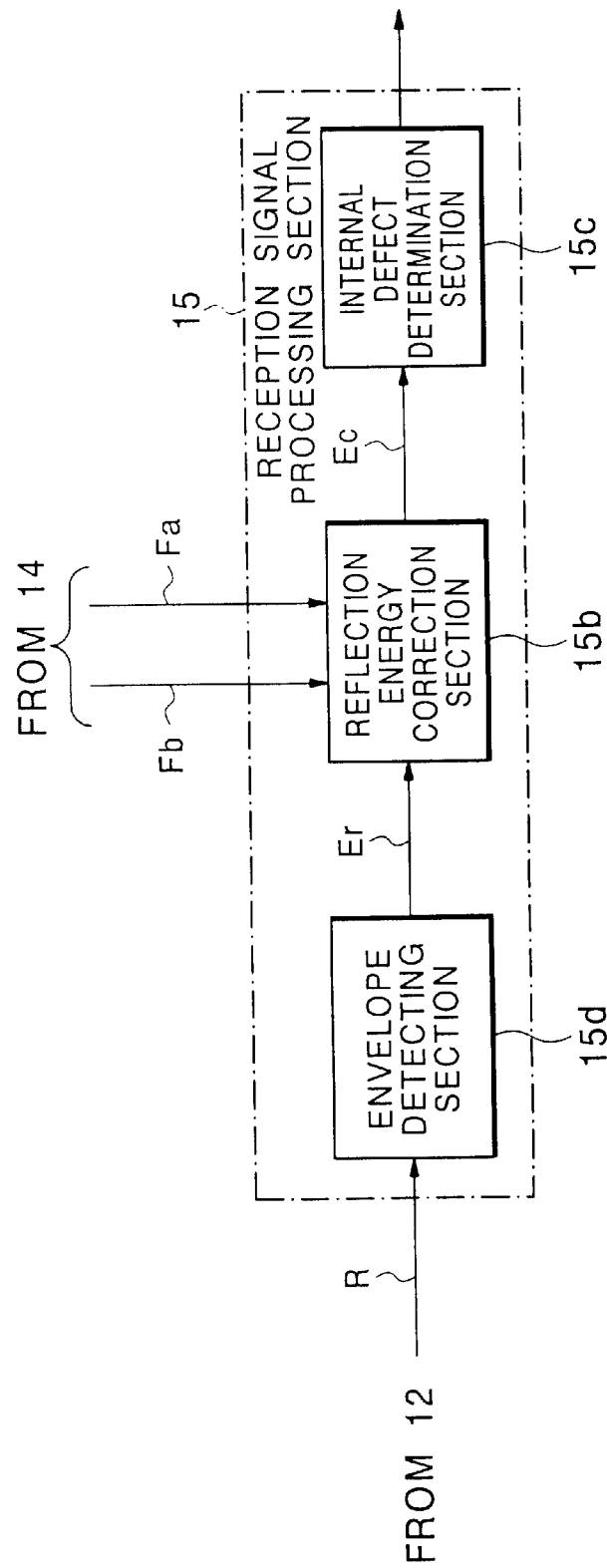
FIG. 8 is a block diagram illustrating a reception signal processing section according to the second embodiment of the present invention.

FIG. 8 is a block diagram illustrating a reception signal processing section 15 for processing a reception signal R based on a reflection wave of the chirp wave, wherein the same or like components as those in the aforementioned embodiment (see FIG. 4) are identified by the same symbols while omitting a detailed description thereof.

In FIG. 8, an envelope detecting section 15d corresponds to the above-mentioned reflection energy calculation section 15a, and serves to calculate an envelope of the reception signal R as a reflection energy level, which is input to the reflection energy correction section 15b.

Now, reference will be made to the operation of the second embodiment of the present invention while referring to FIG. 6 through FIG. 8 along with FIG. 1 and FIG. 3.

First of all, the chirp wave generation section 10c in the vibration control section 10 inputs a drive signal W (chirp wave), of which the frequency continuously rises with the lapse of time, to the power amplifier 10b, and the power amplifier 10b properly amplifies the current waveform of the chirp wave and imposes it on the vibrating section 11 for driving thereof.

The magnetostrictive vibrator 11a of the vibrating section 11 (see FIG. 3) generates a distortion according to the current waveform of the imposed drive signal W, whereby an acoustic elastic wave, of which the frequency rises (or lowers) continuously with time t, is injected into a measuring object 16 at a constant magnitude from the surface of the measuring object 16 which is contacted by the magnetostrictive vibrator 11a.

In this manner, in cases where vibration due to the acoustic elastic wave is given to the measuring object 16, the amplitude of the waveform of the reception signal R observed by the receiving section 12 becomes great when the excitation or vibration frequency is consistent with a natural resonance frequency of the measuring object 16, whereas the amplitude of the waveform of the reception signal R for the frequencies other than this becomes small. That is, the waveform of the reception signal R, of which the amplitude level varies according to the response characteristic of the natural vibration of the measuring object 16, is observed by the receiving section 12.

Since the variation in the amplitude level is proportional to the frequency response of the measuring object 16, a frequency response waveform inherent to the measuring object 16 is obtained by calculating the envelope of the waveform of the observed reception signal R.

The resonance frequency inherent to the measuring object 16 is observed as a predominant frequency as seen in the frequency response, so that one can know the form of vibration at the measuring surface by extracting a peak frequency of the reception signal R. Accordingly, the internal defect 17 in the measuring object 16 and its structure per se can be estimated from the envelope of the waveform of the reception signal R, and discrimination can be easily made between a normal portion and an abnormal portion of the measuring object 16.

In FIG. 8, the envelope detecting section 15d calculates the envelope of the reception signal R from the receiving section 12 as the reflection energy level Er. The envelope of the reception signal R represents the frequency response waveform of the measuring object 16. Thereafter, the internal defect 17 can be determined based on the reflection energy level correction value Ec corrected by the pushing forces F.

In this manner, by calculating the envelope of the reception signal R as the reflection energy level Er by the use of an acoustic elastic wave comprising a chirp wave as a vibration wave, the frequency response waveform can be obtained without performing complicated signal processing such as FFT (Fast Fourier Transform) by simple and convenient calculation processing.

Therefore, it is possible to shorten the processing time to a substantial extent, make wider the inspection area to be inspected within a prescribed period of time, and reduce the size or scale of the measuring equipment for labor saving.

Embodiment 3

Although in the above-mentioned first and second embodiments, no reference has been made to any concrete parameter which is an object for determining the internal defect 17, the distance to the internal defect 17 for example may be made such a determination object.

Figure 9:
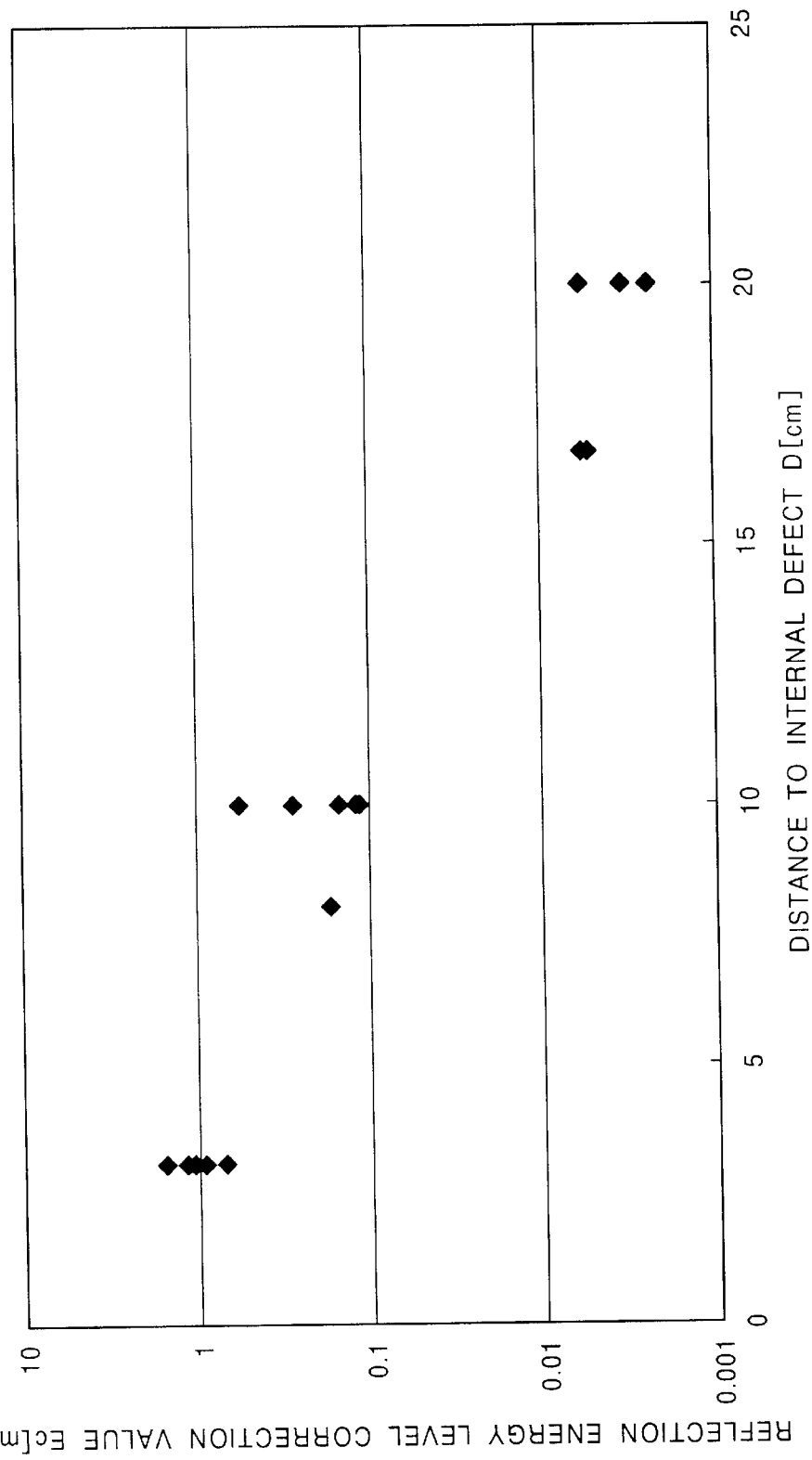
FIG. 9 is a characteristic view illustrating the correlation between the distance to an internal defect detected and a reflection energy level correction value in relation to a third embodiment of the present invention.

FIG. 9 is a characteristic view illustrating the correlation between the reflection energy level correction value Ec and the distance D to the internal defect actually measured in relation to a third embodiment of the present invention, wherein the correlation is stored in advance in the internal defect determination section 15c as map data of the measurement values corresponding to the measuring object 16.

In FIG. 9, the axis of abscissa represents the distance D to the internal defect (the thickness of a peeled-off portion, the depth of a crack, etc., measured at the surface of the measuring object 16), and the axis of ordinate represents the reflection energy level correction value Ec.

The characteristic of FIG. 9 is obtained by acquiring a cross sectional structure at a measurement location of the measuring object 16 by coring a concrete structure for instance, actually measuring the distance D to the internal defect 17 (the depth of a crack, etc.), and actually measuring the reflection energy level Er at the measurement location thereby to calculate a correction value Ec which is normalized by the pushing forces F during vibration.

As described above, the acoustic elastic wave injected from the vibrating section 11 diffuses while being attenuated by the damping effect during propagation through the measuring object 16, but in this attenuation diffusion process, the influences of attenuation and diffusion are reduced more greatly for an internal defect 17 (crack or void) near the measuring surface than for the ones far away therefrom since the distance of propagation of the acoustic elastic wave becomes shorter for the former than for the latter.

Therefore, the reflected wave from the internal defect 17 near the measurement surface is detected with a greater amplitude than that with which the reflected wave from the internal defect 17 far from the measurement surface is detected, so the reflection energy level correction value Ec changes in inverse proportion to the distance D to the internal defect 17, as shown in FIG. 9.

The internal defect determination section 15c stores the characteristic of FIG. 9 measured in advance or an approximate expression corresponding to the characteristic of FIG. 9, and calculates the distance D to the internal defect 17 through estimation by using the reflection energy level correction value Ec normalized by the pushing forces F and the correlation of FIG. 9 (approximate expression).

Incidentally, note that the correlation of FIG. 9 is varied depending on the constituent materials of the measuring object 16, the mixing ratio of the materials, etc., and hence measurements are carried out in advance to clarify the correlation according to variation in the measuring object 16.

In this manner, by storing in advance the correlation between the distance D to the internal defect 17 and the reflection energy level correction value Ec (FIG. 9), it is possible to calculate the distance D to the internal defect 17 by collating the measurement result of the reflection energy level correction value Ec with the characteristic of FIG. 9. Thus, the internal defect determination section 15c can inform the operator of not only the presence or absence of the internal defect 17 but also the distance D to the internal defect 17.

Embodiment 4

Although in the above-mentioned third embodiment, the distance D to the internal defect 17 has been calculated based on the reflection energy level correction value Ec corrected only by the pushing forces F, such a distance D to the internal defect 17 may be calculated based on an additional correction value Ecc that is obtained by further correcting the reflection energy level correction value Ec through division by the magnitude of the internal defect 17 (the area of a measurement region).

Figure 10:
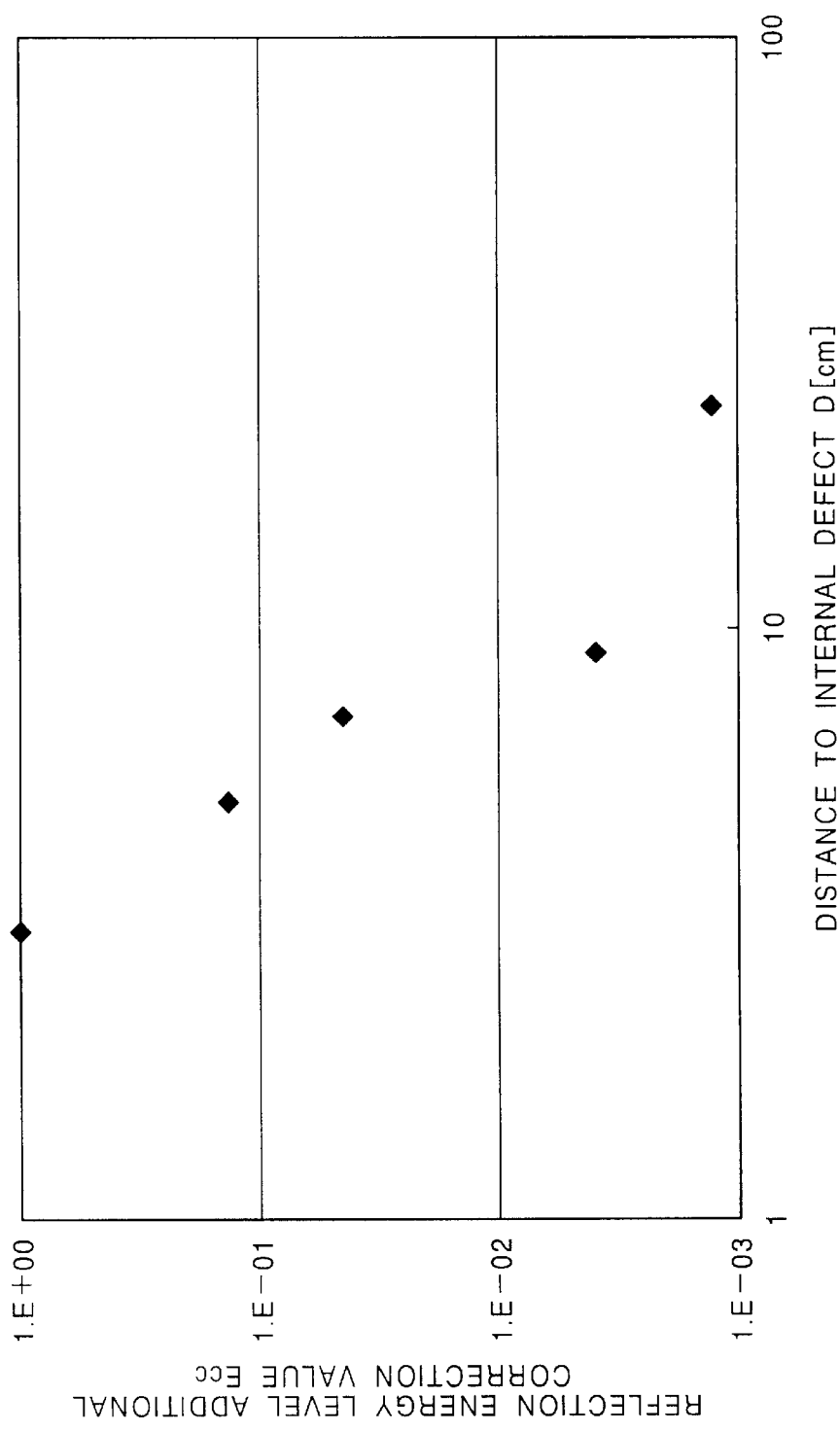
FIG. 10 is a characteristic view illustrating the correlation between the distance to an internal defect measured and a reflection energy level additional correction value in relation to a fourth embodiment of the present invention.

FIG. 10 is a characteristic view illustrating the correlation between the distance D to the internal defect actually measured and the reflection energy level additional correction value Ecc in relation to a fourth embodiment of the present invention, wherein the correlation is stored in advance in the internal defect determination section 15c as map data of the actual measurement values corresponding to the measuring object 16.

In FIG. 10, the axis of abscissa represents the distance D to the internal defect, and the axis of ordinate represents the reflection energy level additional correction value Ecc.

The characteristic of FIG. 10 is obtained through actual measurements after coring as referred to above, and the area of the internal defect 17 is obtained as a region indicative of the existence of the internal defect 17 by repeatedly acquiring the reception signal R while moving the vibrating section 11 over the surface of the measuring object 16.

In this case, the reflection energy correction section 15b corrects the reflection energy level Er measured at the surface of the measuring object 16 by the pushing forces F during vibration, and calculates an additional correction value Ecc by dividing the thus corrected reflection energy level Er by the area of the part where the internal defect 17 (peeling off) has been developed.

The greater the area S of the internal defect 17, the greater becomes the above-mentioned reflection energy level correction value Ec, even though the distance D to the internal defect 17 in the measuring object 16 of the same materials is constant.

Accordingly, in addition to the reflection energy level correction value Ec, the reflection energy level additional correction value Ecc, which is obtained by additionally correcting the reflection energy level correction value Ec through division thereof by the area S of the internal defect 17, has a higher correlation with respect to the distance D to the internal defect 17.

That is, by dividing the above-mentioned reflection energy level correction value Ec (see FIG. 9) by the area S in which the internal defect 17 takes place, the characteristic of FIG. 10 is acquired, thus making it possible to estimate the distance D to the internal defect 17 based on the characteristic of FIG. 10 with further high accuracy.

In this manner, the distance D to the internal defect 17 can be accurately calculated by further dividing the reflection energy level correction value Ec by the area S of the internal defect 17 to calculate the additional correction value Ecc and collating the correlation of FIG. 10 determined in advance.

Since the correlation of FIG. 10 is varied depending on the materials, the mixing ratio or the like of the measuring object 16 as referred to above, the above-mentioned measurement is performed in order to clarify the actual correlation.

Although in above-mentioned first through fourth embodiments, the description has been made by taking as an example the case in which an acoustic elastic wave generated by a magnetostriction phenomenon is injected into the measuring object 16 by using the vibrating section 11 with the magnetostrictive vibrator 11a, it goes without saying that the vibrating section 11 is not limited to the magnetostrictive type, but may be of the piezoelectric type, electrodynamic type or the like while providing the same operation and effects as referred to above.

Also, the description has been given to an example in which the measuring object 16 is a concrete structure, but it is needless to say that the present invention is applicable to other structures with the same operation and effects as described above.

INDUSTRIAL APPLICABILITY

As described in the foregoing, the present invention resides in a nondestructive inspection apparatus for diagnosing an internal defect of a measuring object by injecting an acoustic elastic wave into the measuring object. The apparatus comprises: a vibrating section which is adapted to be placed in pressure contact with a surface of the measuring object for generating the acoustic elastic wave; a receiving section which is adapted to be placed in pressure contact with a surface of the measuring object for receiving a reflected wave of the acoustic elastic wave; a pushing mechanism for pushing the vibrating section and the receiving section against the surface of the measuring object; a pushing force measurement section for detecting pushing forces of the vibrating section and the receiving section against the surface of the measuring object during vibration thereof; a vibration control section for driving the vibrating section thereby to generate the acoustic elastic wave; and a reception signal processing section for determining the internal defect based on the reception signal from the receiving section. The reception signal processing section comprises: a reflection energy calculation section for calculating a reflection energy level due to elasticity vibration of the measuring object based on the reception signal; a reflection energy correction section for normalizing the reflection energy level by the pushing force to calculate a correction value; and an internal defect determination section for detecting the internal defect based on the correction value. With this arrangement, it is possible to determine the absolute reflection energy level of the reflected wave through comparison irrespective of the surface condition of the measuring object, thus improving accuracy in the evaluation of the internal defect or flaw to a substantial extent.

In addition, the vibrating section according to the nondestructive inspection apparatus of the present invention includes a magnetostrictive vibrator for generating the acoustic elastic wave through a magnetostriction phenomenon. Thus, the acoustic elastic wave can be easily injected into the measuring object.

Moreover, the acoustic elastic wave according to the nondestructive inspection apparatus of the present invention comprises a chirp wave with its frequency continuously changing with time; the reception signal processing section includes an envelope detecting section for determining an envelope of elasticity vibration caused by the reflection of the chirp wave, the envelope detecting section being operable to calculate, based on the envelope, a resonance frequency according to a natural oscillation characteristic of the measuring object; and the internal defect determination section detects the internal defect based on the resonance frequency and a response waveform of the supply frequency. With this arrangement, a frequency response waveform can be obtained through simple and convenient processing without performing complicated signal processing such as FFT, whereby it is possible to shorten the processing time and realize reduction in scale of the measuring equipment as well as labor saving.

Further, the internal defect determination section according to the nondestructive inspection apparatus of the present invention calculates a distance to the internal defect based on a correlation between a distance to the internal defect and the correction value which is prepared in advance. Accordingly, it is possible to detect not only the presence or absence of an internal defect but also the distance to the internal defect.

Furthermore, the correlation between the distance to the internal defect and the correction value according to the nondestructive inspection apparatus of the present invention is stored in advance in the internal defect determination section as map data of actual measurement values corresponding to the measuring object. Thus, the correlation with high accuracy can be obtained without regard to variations in the measuring objects, thereby making it possible to further improve reliability in the result of determination of the internal defect.

Still further, the reflection energy correction section according to the nondestructive inspection apparatus of the present invention calculates an additional correction value by dividing the correction value by an abnormal range area of the internal defect; and the internal defect determination section calculates the distance to the internal defect based on a correlation between the distance to the internal defect and the additional correction value which is prepared in advance. Accordingly, the distance to the internal defect can be detected with further high accuracy.

Besides, the correlation between the distance to the internal defect and the additional correction value according to the nondestructive inspection apparatus of the present invention is stored in advance in the internal defect determination section as map data of actual measurement values corresponding to the measuring object. Thus, it is possible to obtain the correlation with high accuracy irrespective of variations in the measuring objects, whereby reliability in the result of determination of the internal defect can be further improved.

Moreover, the measuring object according to the nondestructive inspection apparatus of the present invention comprises a concrete structure. Thus, internal defects or flaws can be effectively determined in particular for general buildings.

What is claimed is:

1. A nondestructive inspection apparatus for diagnosing an internal defect of a measuring object by injecting an acoustic elastic wave into said measuring object, said apparatus comprising:
    a vibrating section which is adapted to be placed in pressure contact with a surface of said measuring object for generating said acoustic elastic wave;
    a receiving section which is adapted to be placed in pressure contact with the surface of said measuring object for receiving a reflected wave of said acoustic elastic wave;
    a pushing mechanism for pushing said vibrating section and said receiving section against the surface of said measuring object;
    a pushing force measurement section for detecting pushing forces of said vibrating section and said receiving section against the surface of said measuring object during vibration thereof;
    a vibration control section for driving said vibrating section thereby to generate said acoustic elastic wave; and
    a reception signal processing section for determining said internal defect based on a reception signal from said receiving section;

wherein said reception signal processing section comprises:
        a reflection energy calculation section for calculating a reflection energy level due to elasticity vibration of said measuring object based on said reception signal;
        a reflection energy correction section for normalizing said reflection energy level by said pushing forces to calculate a correction value; and
        an internal defect determination section for detecting said internal defect based on said correction value.

2. The nondestructive inspection apparatus according to claim 1, wherein said vibrating section includes a magnetostrictive vibrator for generating said acoustic elastic wave through a magnetostriction phenomenon.

3. The nondestructive inspection apparatus according to claim 1, wherein said acoustic elastic wave comprises a chirp wave having a frequency continuously changing with time;
    said reception signal processing section includes an envelope detecting section for determining an envelope of elasticity vibration caused by the reflection of said chirp wave, said envelope detecting section being operable to calculate, based on said envelope, a resonance frequency according to a natural oscillation characteristic of said measuring object; and
    said internal defect determination section detects said internal defect based on said resonance frequency and a response waveform of a supply frequency of the vibrating section.

4. The nondestructive inspection apparatus according to claim 1, wherein said internal defect determination section calculates a distance to said internal defect based on a correlation between a distance to said internal defect and said correction value which is prepared in advance.

5. The nondestructive inspection apparatus according to claim 4, wherein the correlation between the distance to said internal defect and said correction value is stored in advance in said internal defect determination section as map data of actual measurement values corresponding to said measuring object.

6. The nondestructive inspection apparatus according to claim 1, wherein said reflection energy correction section calculates an additional correction value by dividing said correction value by an abnormal range area of said internal defect; and
    said internal defect determination section calculates the distance to said internal defect based on a correlation between the distance to said internal defect and said additional correction value which is prepared in advance.

7. The nondestructive inspection apparatus according to claim 6, wherein the correlation between the distance to said internal defect and said additional correction value is stored in advance in said internal defect determination section as map data of actual measurement values corresponding to said measuring object.

8. The nondestructive inspection apparatus according to claim 1, wherein said measuring object comprises a concrete structure.

9. A nondestructive inspection apparatus for diagnosing an internal defect of a measuring object by injecting an acoustic elastic wave into said measuring object, said apparatus comprising:
    a vibrating means for generating said acoustic elastic wave;
    a receiving means for receiving a reflected wave of said acoustic elastic wave;

a pushing means for pushing said vibrating means and said receiving means against the surface of said measuring object;

a pushing force measurement means for detecting pushing forces of said vibrating means and said receiving means against the surface of said measuring object during vibration thereof;

a vibration control means for driving said vibrating means so as to generate said acoustic elastic wave; and a reception signal processing means for determining said internal defect based on a reception signal from said receiving means;

wherein said reception signal processing means comprises:

a reflection energy calculation means for calculating a reflection energy level due to elasticity vibration of said measuring object based on said reception signal;

a reflection energy correction means for normalizing said reflection energy level by said pushing forces to calculate a correction value; and an internal defect determination means for detecting said internal defect based on said correction value.

10. The nondestructive inspection apparatus according to claim 9, wherein said vibrating means includes a magnetostrictive vibrator for generating said acoustic elastic wave through a magnetostriction phenomenon.

11. The nondestructive inspection apparatus according to claim 9, wherein said acoustic elastic wave comprises a chirp wave having a frequency continuously changing with time;

said reception signal processing means includes an envelope detecting means for determining an envelope of elasticity vibration caused by the reflection of said chirp wave, said envelope detecting means being operable to calculate, based on said envelope, a resonance frequency according to a natural oscillation characteristic of said measuring object; and said internal defect determination means detects said internal defect based on said resonance frequency and a response waveform of a supply frequency of the vibrating means.

12. The nondestructive inspection apparatus according to claim 9, wherein said internal defect determination means calculates a distance to said internal defect based on a correlation between a distance to said internal defect and said correction value which is prepared in advance.

13. The nondestructive inspection apparatus according to claim 12, wherein the correlation between the distance to said internal defect and said correction value is stored in advance in said internal defect determination means as map data of actual measurement values corresponding to said measuring object.

14. The nondestructive inspection apparatus according to claim 9, wherein said reflection energy correction means calculates an additional correction value by dividing said correction value by an abnormal range area of said internal defect; and said internal defect determination means calculates the distance to said internal defect based on a correlation between the distance to said internal defect and said additional correction value which is prepared in advance.

15. The nondestructive inspection apparatus according to claim 14, wherein the correlation between the distance to said internal defect and said additional correction value is stored in advance in said internal defect determination means as map data of actual measurement values corresponding to said measuring object.

16. The nondestructive inspection apparatus according to claim 9, wherein said measuring object comprises a concrete structure.

* * * * *